(12) United States Patent
Yang et al.

(10) Patent No.: US 12,377,117 B2
(45) Date of Patent: Aug. 5, 2025

(54) HYALURONIC ACID NANOPARTICLES COMPRISING NADPH OXIDASES INHIBITORS AND USES IN TREATING CANCER

(71) Applicant: Emory University, Atlanta, GA (US)

(72) Inventors: Lily Yang, Atlanta, GA (US); Lei Zhu, Atlanta, GA (US)

(73) Assignee: Emory University, Atlanta, GA (US)

( * ) Notice: Subject to any disclaimer, the term of this patent is extended or adjusted under 35 U.S.C. 154(b) by 816 days.

(21) Appl. No.: 17/600,935

(22) PCT Filed: Apr. 1, 2020

(86) PCT No.: PCT/US2020/026120
§ 371 (c)(1),
(2) Date: Oct. 1, 2021

(87) PCT Pub. No.: WO2020/205937
PCT Pub. Date: Oct. 8, 2020

(65) Prior Publication Data
US 2022/0193117 A1 Jun. 23, 2022

Related U.S. Application Data

(60) Provisional application No. 62/827,325, filed on Apr. 1, 2019.

(51) Int. Cl.
*A61K 31/728* (2006.01)
*A61K 9/51* (2006.01)
*A61K 31/437* (2006.01)
*A61K 47/69* (2017.01)
*A61P 35/00* (2006.01)

(52) U.S. Cl.
CPC .......... *A61K 31/728* (2013.01); *A61K 9/5161* (2013.01); *A61K 31/437* (2013.01); *A61K 47/6939* (2017.08); *A61P 35/00* (2018.01)

(58) Field of Classification Search
CPC .... A61K 31/728; A61K 47/26; A61K 47/554; A61P 35/00
See application file for complete search history.

(56) References Cited

U.S. PATENT DOCUMENTS

| | | | |
|---|---|---|---|
| 2015/0147276 A1 | 5/2015 | Ingber | |
| 2015/0231268 A1* | 8/2015 | Nakai | A61K 47/61 536/53 |
| 2016/0310608 A1 | 10/2016 | Yang | |
| 2017/0173169 A1 | 6/2017 | Yantasee | |
| 2017/0326141 A1 | 11/2017 | Trower | |
| 2018/0280290 A1 | 10/2018 | Popov | |
| 2021/0177811 A1* | 6/2021 | Wiesel | A61P 35/00 |

FOREIGN PATENT DOCUMENTS

| | | |
|---|---|---|
| WO | 2010035221 | 4/2010 |
| WO | 2016043690 | 3/2016 |
| WO | 2019086579 | 5/2019 |

OTHER PUBLICATIONS

Bertrand et al. Cancer Nanotechnology: The impact of passive and active targeting in the era of modern cancer biology, Adv Drug Deliv Rev. 2014, 66: 2-25.
Carlsson, A Trial of Setanaxib in Patients with Primary Biliary Cholangitis (PBC) and Liver Stiffness (TRASFORM), 2021, NCT05014672, Availalbe at ClinicalTrials.gov.
Choi et al. Self-assembled hyaluronic acid nanoparticles for active tumor targeting, Biomaterials 31 (2010) 106-114.
Cifuentes-Pagano et al. Nox Inhibitors & Therapies: Rational Design of Peptidic and Small Molecule Inhibitors, Curr Pharm Des. 2015, 21(41): 6023-6035.
Duan et al. Photodynamic Therapy Mediated by Nontoxic Core-Shell Nanoparticles Synergizes with Immune Checkpoint Blockade To Elicit Antitumor Immunity and Antimetastatic Effect on Breast Cancer, J Am Chem Soc. 2016, 138(51): 16686-16695.
Elsey et al. Palladium based nanoparticles for the treatment of advanced melanoma, Scientific Reports, 2019, 9:3255.
Ford et al. NOX4 Inhibition Potentiates Immunotherapy by Overcoming Cancer-Associated Fibroblast-Mediated CD8 T-cell Exclusion from Tumors, Cancer Res, 2020, 80(9):1846-1860.
Genkyotex, Genkyotex's setanaxib significantly improves immunotherapy including checkpoint inhibitors in multiple preclinical cancer models, Press Release, Archamps (France), Mar. 3, 2020 at 6:00 pm CET.
Hanley et al., Targeting the Myofibroblastic Cancer-Associated Fibroblast Phenotype Through Inhibition of NOX4, JNCI J Natl Cancer Inst (2018) 110(1):109-120.
He et al. Core-shell nanoscale coordination polymers combine chemotherapy and photodynamictherapy to potentiate checkpoint blockade cancer immunotherapy, Nature Communications, 2016, 7:12499.
Sampson et al. Inhibition of Nox4-dependent ROS signaling attenuates prostate fibroblast activation and abrogates stromal-mediated protumorigenic interactions, Int. J. Cancer: 143, 383-395 (2018).
Zeng et al., NOX4 supports glycolysis and promotes glutamine metabolism in nonsmall cell lung cancer cells, Free Radical Biology and Medicine 101 (2016) 236-248.
Zhu et al. NADPH oxidases 4 inhibition using a hyaluronic acid nanoparticle drug delivery system sensitized therapeutic response to chemo and radiotherapy in drug resistant breast cancer, In: Proceedings of the American Association for Cancer Research Annual Meeting 2019; AACR; Cancer Res 2019;79(13 Suppl):Abstract nr 3933.

* cited by examiner

*Primary Examiner* — Pancham Bakshi
(74) *Attorney, Agent, or Firm* — Emory Patent Group

(57) ABSTRACT

This disclosure relates to hyaluronic acid nanoparticles containing an anticancer agent such as a NADPH oxidase (NOX) inhibitor for targeted delivery to cancerous cells or tumors. In certain embodiments, the nanoparticles are made up of hyaluronic acid conjugated to hydrophobic moieties. In certain embodiments, the hydrophobic moieties are steroid based compounds, such as 5beta-cholanic acid.

2 Claims, 10 Drawing Sheets
Specification includes a Sequence Listing.

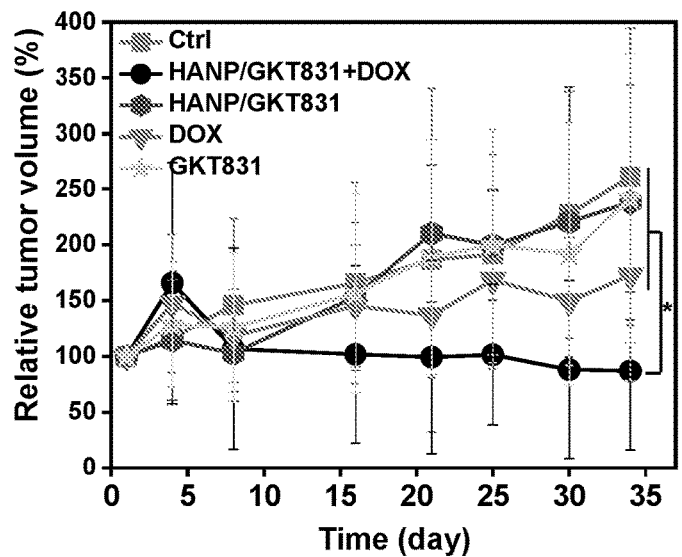
FIG. 3A
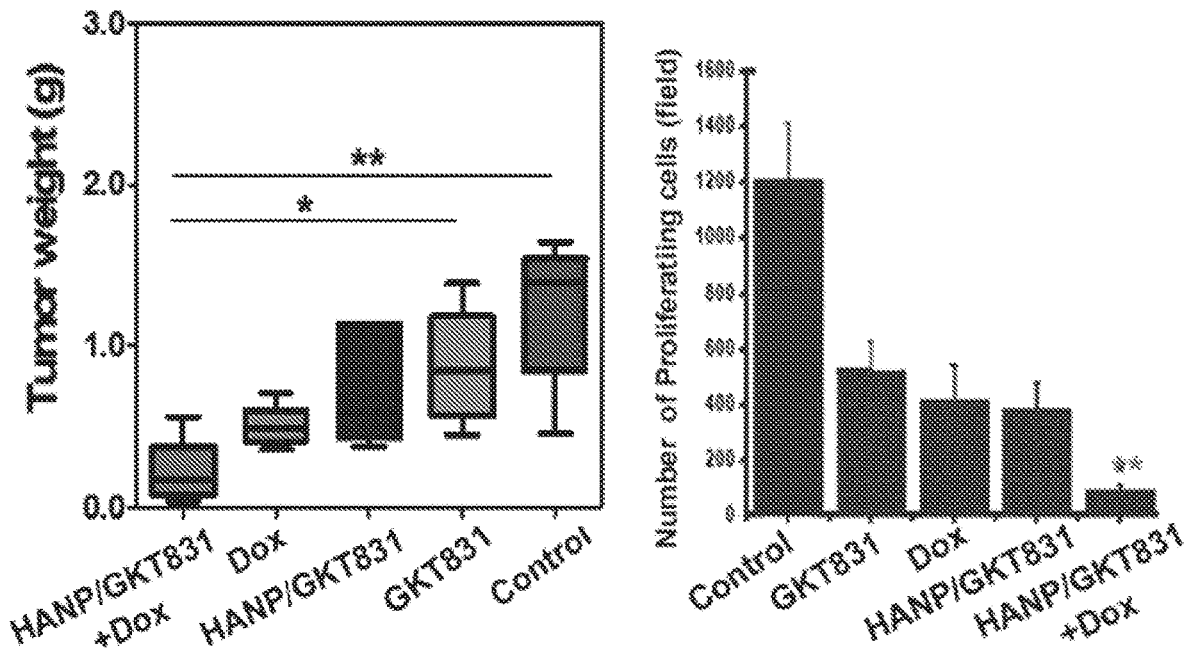
FIG. 3B                                    FIG. 3C

HYALURONIC ACID NANOPARTICLES COMPRISING NADPH OXIDASES INHIBITORS AND USES IN TREATING CANCER

CROSS-REFERENCE TO RELATED APPLICATIONS

This application is the National Stage of International Application No. PCT/US2020/026120, which claims the benefit of U.S. Provisional Application No. 62/827,325 filed Apr. 1, 2019. The entirety of each of these applications is hereby incorporated by reference for all purposes.

STATEMENT REGARDING FEDERALLY SPONSORED RESEARCH OR DEVELOPMENT

This invention was made with government support under CA198913 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19113PCT ST25.txt. The text file is 6 KB, was created on Mar. 31, 2020, and is being submitted electronically via EFS-Web.

BACKGROUND

Current cancer treatments aim to neutralize tumor growth and/or induce the cell death of the malignant cells. Common treatments include; chemotherapy, the use of an anti-cancer agent throughout the entire body, and radiation therapy, exposing localized tumors to harmful radiation. Both of these treatments can damage healthy tissue in addition to the cancer, and as these treatments progress overall health of patients commonly decline. Certain types of cancer have been found to be resistant to treatment further exacerbating the situation. Thus, there is a need for improved cancer therapies.

Ford et al. report NOX4 inhibition using 2-(2-chlorophenyl)-4-[3-(dimethylamino) phenyl]-5-methyl-1H-pyrazolo[4,3-c]pyridine-3,6(2H,5H)-dione (GKT137831) potentiates immunotherapy by overcoming cancer-associated fibroblast-mediated CD8 T-cell exclusion from tumors. Cancer Res 2020, WO 2010/035221, and WO 2019/086579.

Choi et al. report self-assembled hyaluronic acid nanoparticles for active tumor targeting. Biomaterials, 31 (2010) 106-114.

Yang et al. report targeted protease compositions. See U.S. Pub. App. No. 2016/0310608.

References cited herein are not an admission of prior art.

SUMMARY

This disclosure relates to hyaluronic acid nanoparticles containing an anticancer agent such as a NADPH oxidase (NOX) inhibitor for targeted delivery to cancerous cells or tumors. In certain embodiments, the nanoparticles are made up of polysaccharides such as hyaluronic acid conjugated to hydrophobic moieties. In certain embodiments, the hydrophobic moieties are steroid based compounds, such as 5beta-cholanic acid. In certain embodiments, the anti-cancer agent is a NADPH oxidase (NOX) 4 inhibitor such as is setanaxib, 2-(2-chlorophenyl)-4-(3-(dimethylamino)phenyl)-5-methyl-1,2-dihydro-3H-pyrazolo[4,3-c]pyridine-3,6(5H)-dione (GKT831), derivative, or salt thereof.

In certain embodiments, nanoparticles disclosed herein comprise another anti-cancer agent in addition to the NOX inhibitor. In certain embodiments, the anti-cancer agent may be attached to the outer coating of the nanoparticle or incorporated within the core of the nanoparticle.

In certain embodiments, the nanoparticles comprise a targeting molecule linked to the nanoparticle and wherein a catalytic domain of a protease is linked to the nanoparticle. In certain embodiments, the targeting molecule and the catalytic domain are within a single polypeptide sequence. In certain embodiments, the targeting molecule binds a biomolecule more highly expressed on cancer cells when compared non-cancerous cells.

In certain embodiments, this disclosure relates to pharmaceutical compositions comprising nanoparticles disclosed herein and pharmaceutically acceptable excipient. In certain embodiments, the pharmaceutical composition is in the form of a pH buffered aqueous solution or in the form of a gel, tablet, or capsule. In certain embodiments, the pharmaceutically acceptable excipient is lactose, dextrin, glucose, sucrose, or sorbitol.

In certain embodiments, this disclosure relates to methods of treating cancer comprising administering an effective amount of nanoparticles disclosed herein in combination with a cancer treatment to a subject in need thereof. In certain embodiments, the cancer treatment is administering nanoparticle disclosed herein in combination with another anti-cancer agent to the subject. In certain embodiments, the anti-cancer agent is doxorubicin (Dox). In certain embodiments, the nanoparticles are administered prior to, during, or after administration of the cancer treatment. In certain embodiments, the cancer treatment is radiation. In certain embodiments, the cancer is breast, lung, brain, pancreatic, colon, or prostate cancer. In certain embodiments, the subject is human.

BRIEF DESCRIPTION OF THE SEVERAL VIEWS OF THE DRAWING(S)

Figure 1:
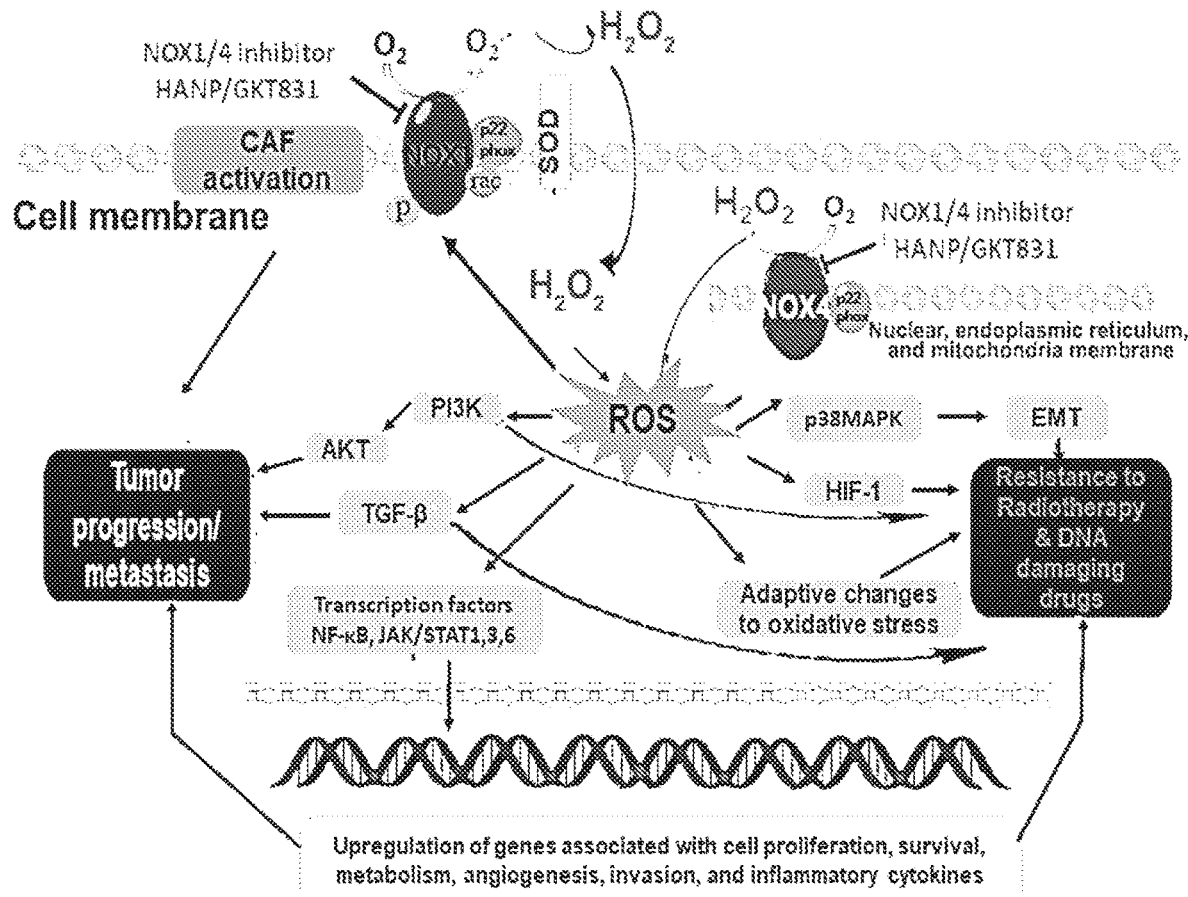
FIG. 1 illustrates mechanisms by which NOX1 and NOX4 induces reactive oxygen species (ROS) thereby activating many important signal pathways that lead to tumor progression and resistance to therapy.
Figure 2A:
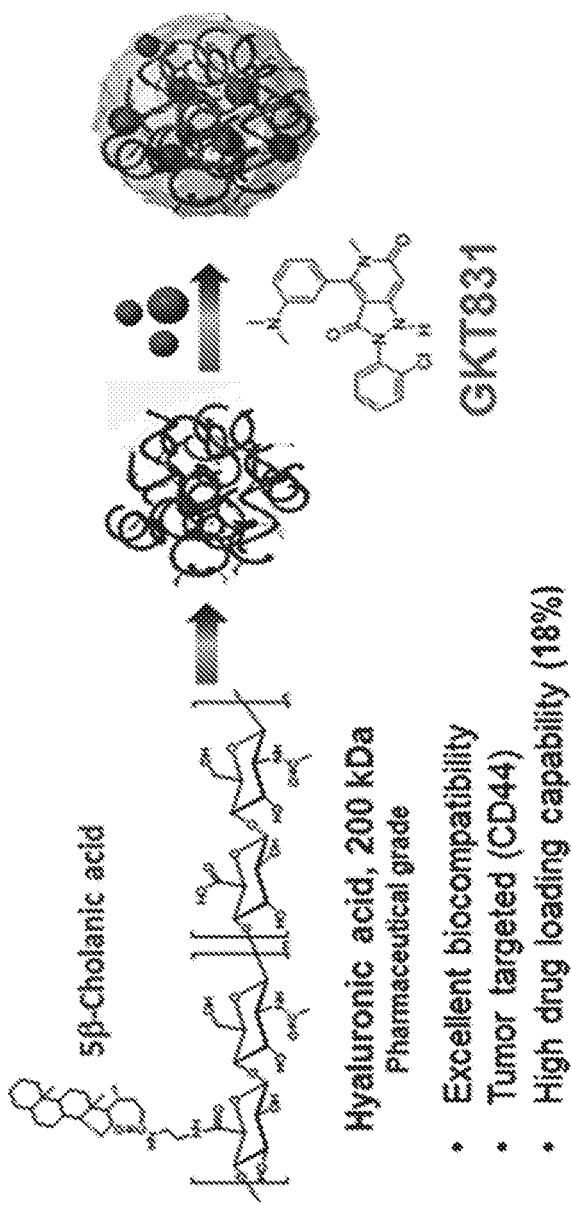
FIG. 2A illustrates conjugating hyaluronic acid (HA) to cholanic acid (HACA) and encapsulation of hydrophobic GKT831 into a hyaluronic acid nanoparticle (HANP).
Figure 2B:
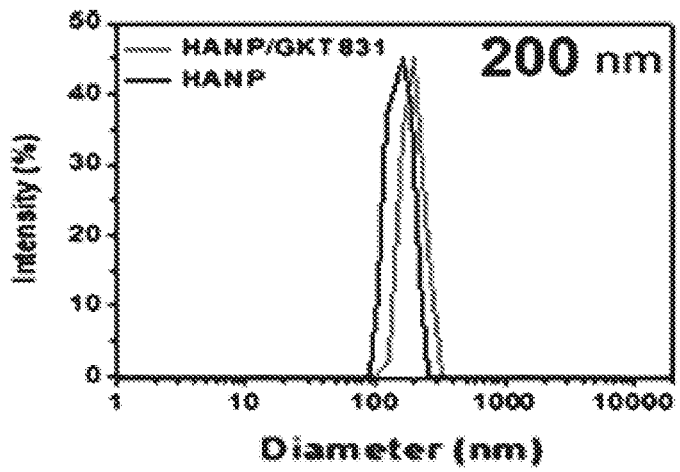
FIG. 2B shows data on the hydrodynamic sizes of HANPs and HANPs containing GKT831 which are about 180±29 and 202±16 nm in diameter respectively.
Figure 2C:
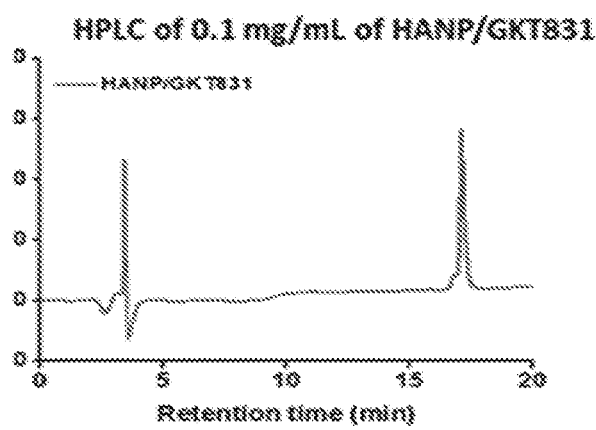
FIG. 2C shows a graph indicating GKT831 loading reached about 18% (w/w) as calculated from HPLC detection.
Figure 2D:
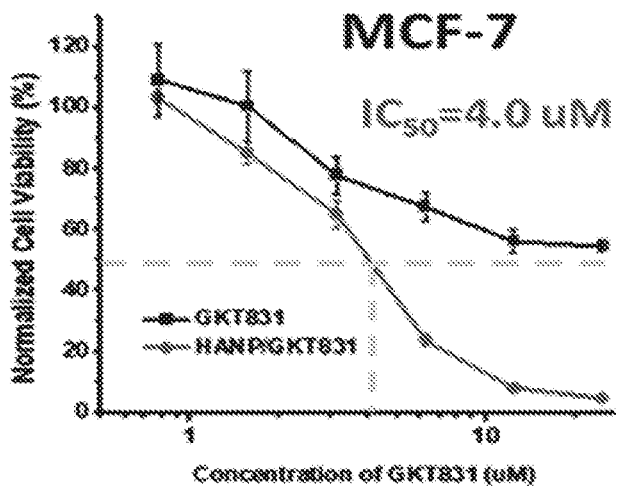
FIG. 2D show data from a cell proliferation assay indicating the ICso of HANP/GKT831 on human breast cancer MCF-7 cells is 4 µM. Free GKT831 had an ICso of 30 µM.
Figure 2E:
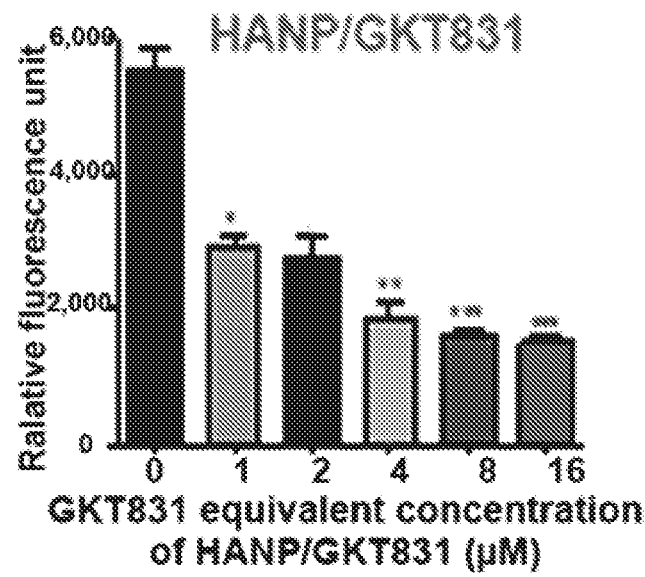
FIG. 2E shows data indicating HANP/GKT831 significantly reduced ROS generation in MCF-7 cells by inhibition of NOX1/4 activity.
Figure 2F:
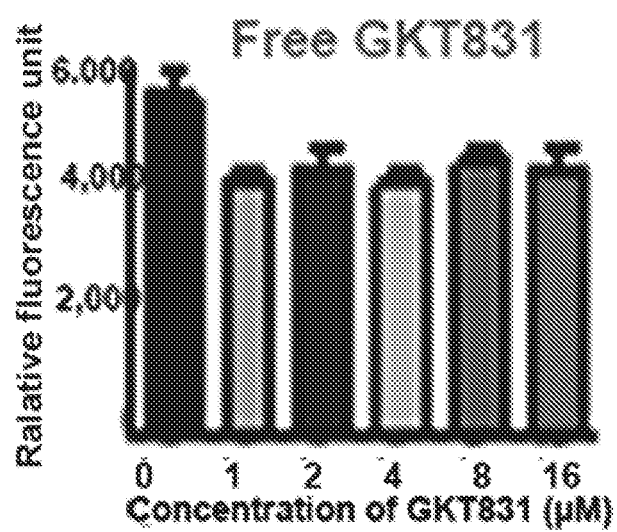

FIG. 2F Non-formulated GKT831 did not show obvious ROS reduction, indicating the combined effect of HANPs and GKT831 are important for a strong inhibitory effect.

FIG. 3A shows tumor growth curves indicating in vivo therapeutic efficacy in breast cancer patient derived xenograft (PDX) models. Nude mice bearing orthotopic the Breast patient VII PDX tumors received 5 mg/kg equivalent dose of GKT831 or HANP/GKT831 combined with 5 mg/kg of DOX via the tail vein once a week for 5 administrations.

FIG. 3B shows data on the mean tumor weight of each mouse group. The minor difference between the tumor volume in the growth curve and the tumor weight is due to the fact that PDX tumors are aggressive and became necrotic. The combination of HANP/GKT831 with DOX showed the strongest anti-tumor effect among the groups.

FIG. 3C shows data on the quantification of proliferating cells in tumor tissue sections after anti-Ki67 antibody labeling.

Figure 3D:
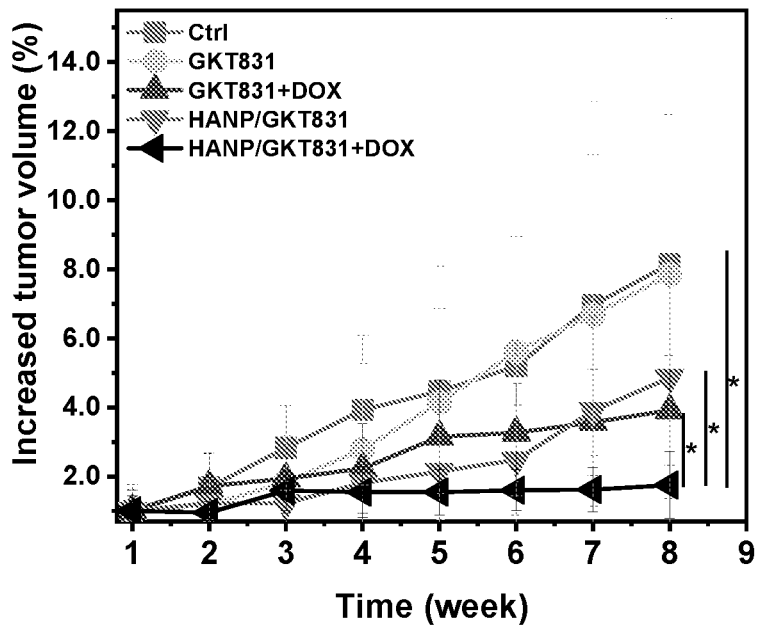
Figure 3E:
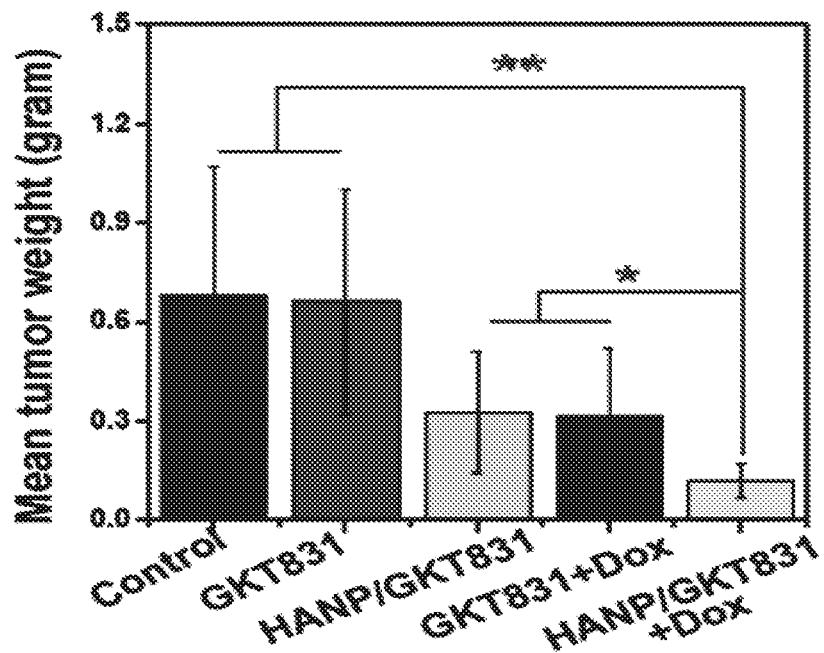

FIG. 3D shows data on tumor growth curves of the Breast patient IX PDX tumors following treatment with HANPs/GKT831 or GKT831, without or with in combination with Dox. Free GKT831 treated did not show any effect on tumor growth. The combination of HANPs/GKT831 with Dox significantly inhibited tumor growth compared with all other treatment groups FIG. 3E shows data on the mean tumor weight of treatment groups. HANP/GKT831+Dox vs no treatment control.

Figure 4A:
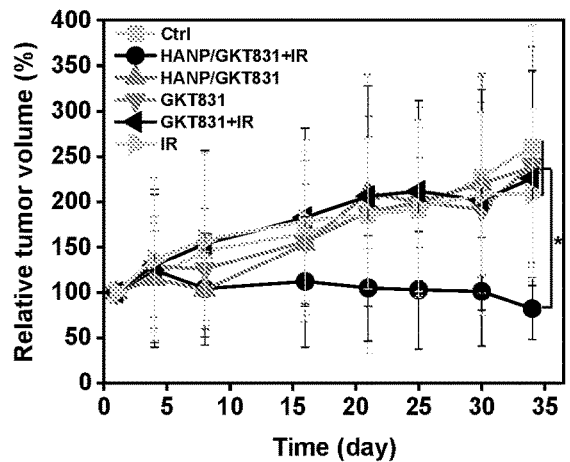

FIG. 4A shows tumor growth curves for a combination therapy of HANP/GKT831 and low dose radiation sensitized breast cancer cells to radiotherapy in a radio-resistant breast cancer PDX model. Nude mice bearing Breast patient VII PDX tumors received i.v. injections of 5 mg/kg equivalent dose of GKT831 or HANPs/GKT831, combined with 2 Gy of radiation at 24 hrs, once per week for 5 treatments. Growth curves show changes in tumor volumes during treatment compared the tumor volumes before the treatment.

Figure 4B:
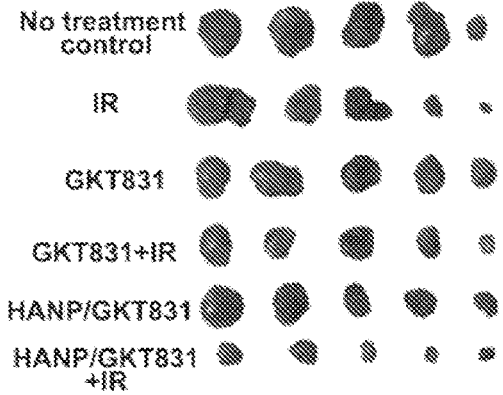

FIG. 4B shows tumor images collected 6 days after the last treatment.

Figure 4C:
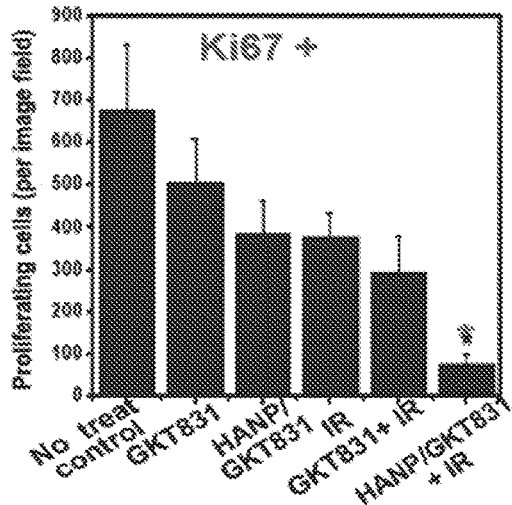

FIG. 4C shows percentage of proliferating cells in tumor tissues. The mean value of 5 to 6 images of the total Ki67 positive cells/image field were used for each group.

Figure 4D:
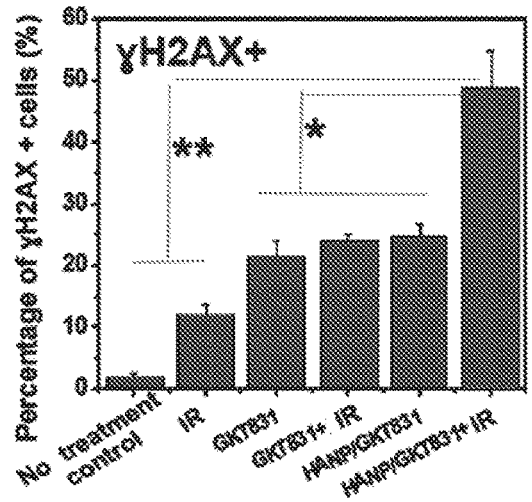

FIG. 4D shows data on the quantification of a DNA-damage biomarker γ-H2AX+ cells in tumor tissues of different treatment groups by immunofluorescence labeling with an anti-γ-H2AX antibody. Images from tumor tissues were used to determine the percentage of γ-H2AX+ cells, a biomarker for DNA double stranded DNA breaks.

Figure 4E:
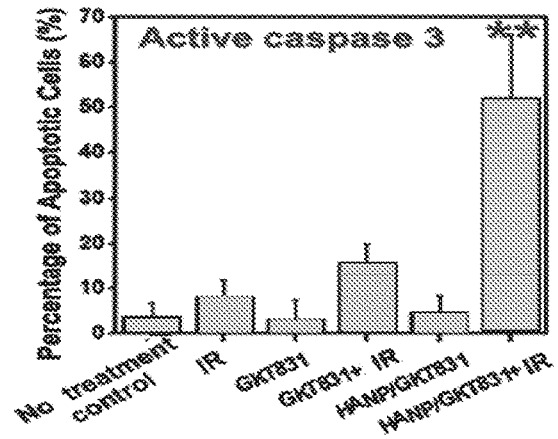

FIG. 4E shows data on the detection of apoptotic cell death by an anti-active caspase 3 antibody. A significant increase in apoptotic cell death was found in HANPs/GKT831 treated tumor tissues, supporting that inhibition of NOX1/4 using HANPs/GKT831 prevents tumor cell growth and sensitizes cells to radiation.

Figure 5:
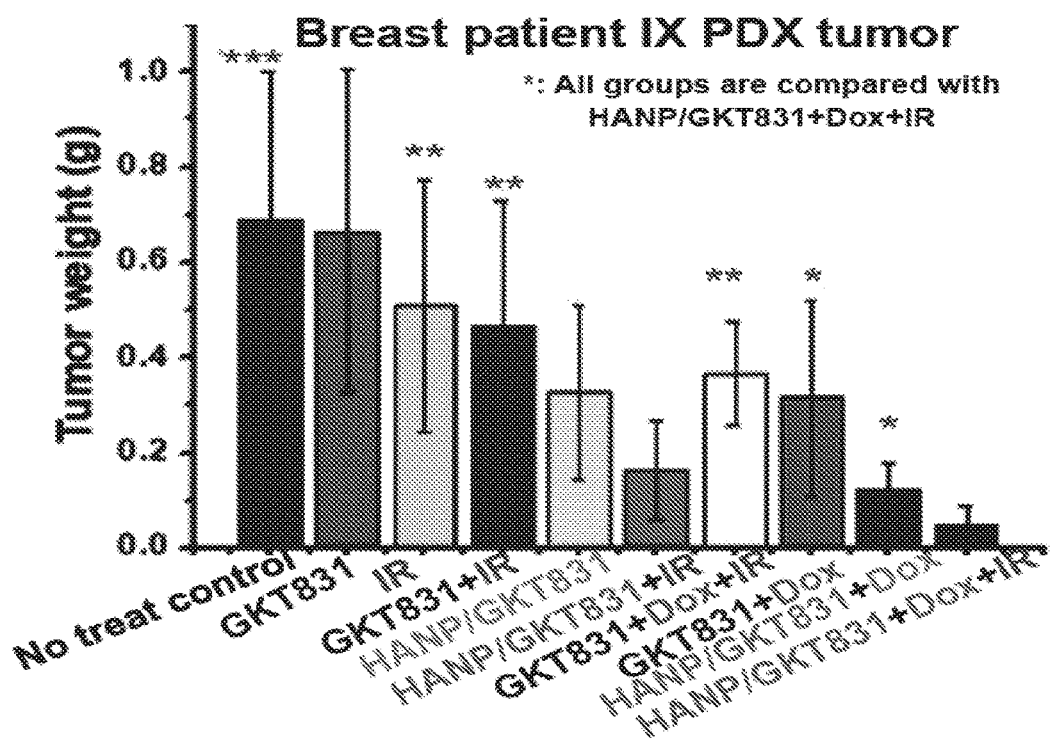

FIG. 5 shows data on the therapeutic effect of the combination therapy of HANPs/GKT831 with Dox, radiation or the co-Dox+(irradiation)IR treatment in the Breast patient IX PDX model. Nude mice received i.v. delivery of 5 mg/kg of GKT831 equivalent dose of HANP/GKT831, without or with 5 mg/kg of Dox, once per week for five treatments. 2 Gy of irradiation was applied to the tumor area 24 hrs after each i.v. drug administration. Tumors were collected 6 days following the last treatment.

Figures 6A, 6B:
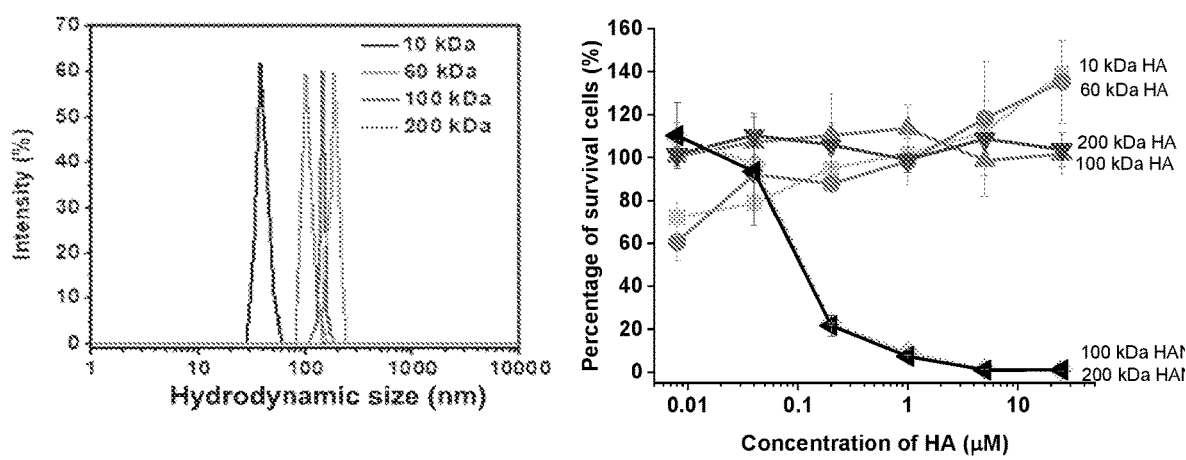

FIG. 6A shows production of size tunable HANPs. Hydrodynamic diameters of HANPs produced from 10, 60, 100 or 200 KDa HA are: 45±13, 100±27, 135±40 and 180±29 nm, respectively.

FIG. 6B shows data from cell proliferation assays on a mouse colon cancer cell line. Effect of native HA fragments and HANPs on cell proliferation and viability in a mouse colon cancer cell line (MC38).

Figure 7A:
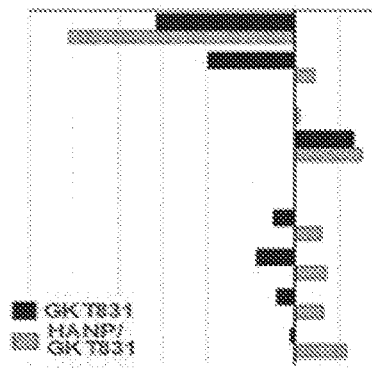

FIG. 7A shows differential effects of non-formulated GKT831 and HANP/GKT831 on selected genes in the NOX and anti-oxidant pathways from RNAseq analysis of human breast PDX tumors after five weekly treatments.

Figure 7B:
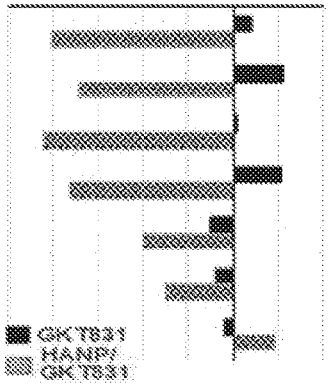

FIG. 7B shows differential effects of non-formulated GKT831 and HANP/GKT831 treatment of human breast PDX tumors on selected genes in the mitochondria complexes for the electron transport chain and ATP production detected by RNAseq, HANP/GKT831 decrease the level of gene expression but GKT831 increased MT-ND and MT-CO2 expression. ATFB was increased by HANP/GKT831 but decrease in GKT831 treated tumor.

Figure 7C:
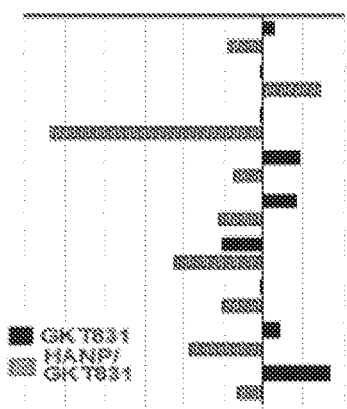

FIG. 7C shows differential effects of non-formulated GKT831 and HANP/GKT831 treatment of human breast PDX tumors on selected DNA repair genes. HANP/GKT831, but not GKT831, significantly inhibited the levels of DNA repair genes, which increased accumulation of DNA damage and H2AX+ tumor cells.

Figure 7D:
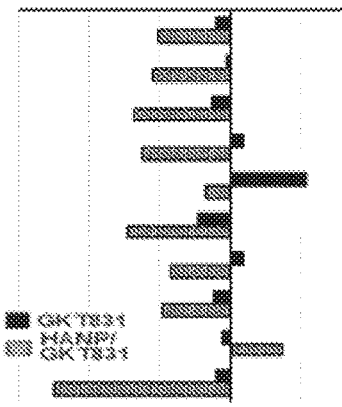
Figure 8:
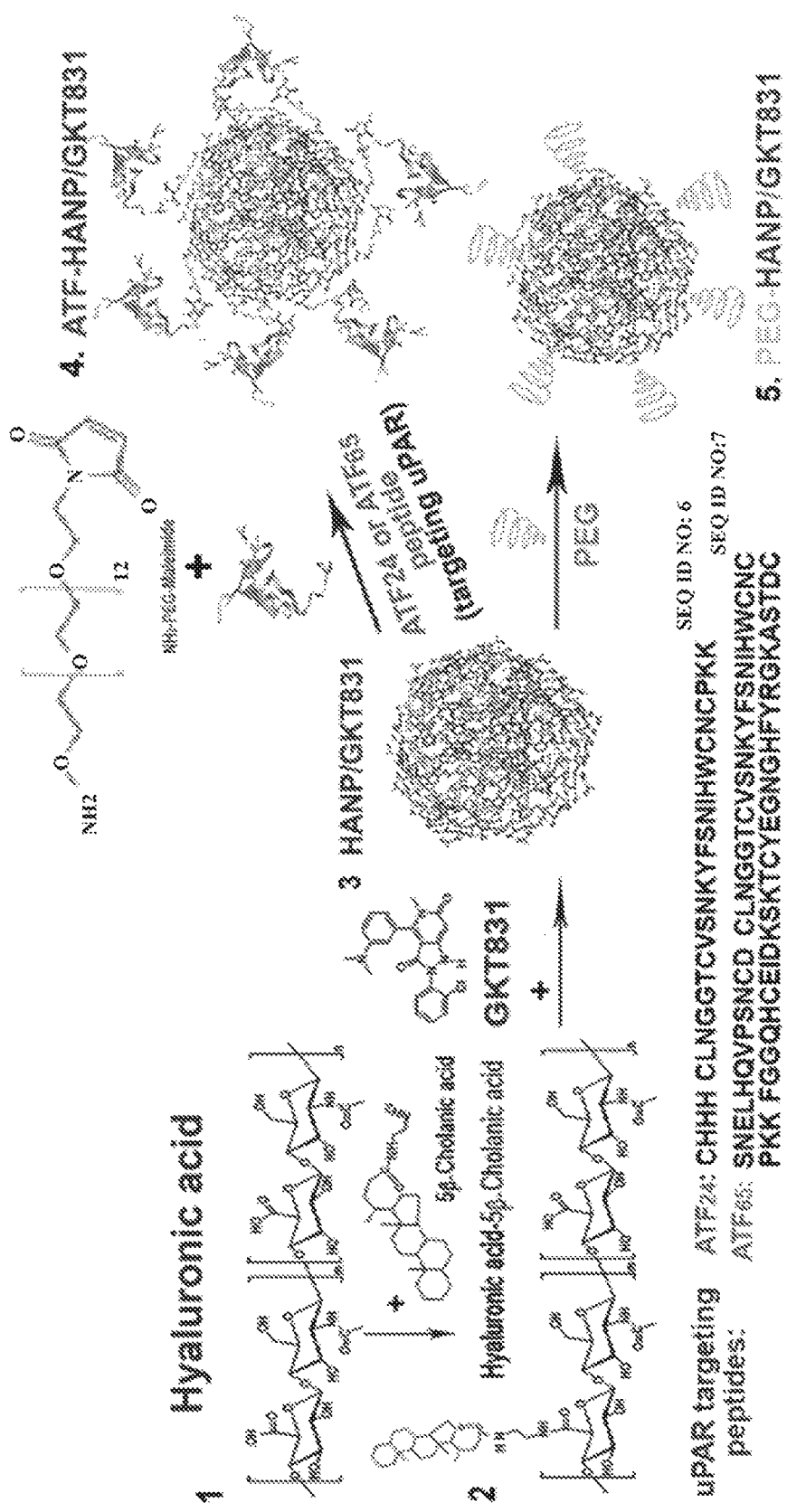

FIG. 7D shows RNAseq result of human breast PDX tumors following treatment. HANP/GKT831, but not GKT831, had stronger inhibition on the levels of oncogenic genes, and growth factors, PI3K pathway, cell proliferation, and survival pathway genes. HANP/GKT831 also increased pro-apoptotic BAX gene FIG. 8 illustrates an engineering ATF peptide conjugated HANPs/GKT831 to improve targeted delivery and biodistribution in tumor and normal tissues. ATF uPAR targeting peptides are conjugated to the exterior surface of the particles. ATF24 contains a N-terminal polyhistidine CHHHCLNGGTCVSNKYFSNIHWCNCPKK (SEQ ID NO: 6). ATF65 is SNELHQVPSNCDCLNGGTCVSNKYFSNIHWCNCPKKFGGQHCEIDK-SKTCYEGNGHFYRGKASTDC (SEQ ID NO: 7). Conjugating mixtures of these peptides to the nanoparticles are contemplated.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, idoxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the terms "peptide," "polypeptide," and "protein" are used interchangeably, and refer to a compound comprised of amino acid residues covalently linked by peptide bonds. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types.

Sequence "identity" refers to the number of matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example, the polypeptides GGGGGG (SEQ ID NO: 8) and GGGGT (SEQ ID NO: 9) have a sequence identity of 4 out of 5 or 80%. For example, the polypeptides GGGPPP (SEQ ID NO: 10) and GGGAPPP (SEQ ID NO: 11) have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

As used herein, the term "derivative" refers to a structurally similar compound that retains sufficient functional attributes of the identified molecule. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxyl group, replacing an aromatic CH with a nitrogen or sulfur. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, alkanoyl, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. $R_a$ and $R_b$ in this context may be the same or different and independently hydrogen, halogen hydroxyl, alkyl, alkoxy, alkanoyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

The term "optionally substituted," as used herein, means that substitution is optional and therefore it is possible for the designated atom to be unsubstituted.

The term "nanoparticle" refers to a molecular conglomerate of an average of about between 10 nm and 10,000 nm of a core diameter or hydrodynamic diameter, or of about between 10 nm and 1,000 nm of a core diameter or hydrodynamic diameter, or of about between 10 nm and 500 nm of a core diameter or hydrodynamic diameter. One more molecules or biomolecules linked to the nanoparticle typically refers to covalently attaching the molecules or biomolecules to a polymer based exterior coating. Hydroxyl groups, amine groups, or thiol groups on the nanoparticle coating provide a place for synthetic attachment of different functional groups. Linking molecules or polypeptides to the polymers can be accomplished using a variety of methods known to skilled artisans. For example, primary amine and thiol containing compounds and proteins may be conjugated to carboxylic acid groups on the polymer mediated by coupling reagents such as EDAC. See Yang et al., Small, 2009, 5(2):235-43, hereby incorporated by reference in its entirety. Other coupling methods are contemplated, e.g., poly-histidine sequence may be recombinantly incorporated into a polypeptide sequence of a targeting molecule. A poly-histidine chelating agent may be coupled to the polymer surface, e.g., NTA-Ni. Mixing the histidine tagged polypeptide sequence attaches it to the polymer surface linked through the chelating agent. Alternatively, ligand and ligand receptor interactions, antibody-antigen/epitope, or avidin/streptavidin-biotin interactions may be used. For example, biotin may be coupled to the polymer surface coating and streptavidin may be expressed as a fusion/chimera with the targeting molecule.

Biodegradable and Bioactive Hyaluronic Acid Nanoparticles (HANP) as Targeted Drug Carriers.

Hyaluronic acid (HA) has affinity for CD44, which is overexpressed in lung, breast, pancreatic, and renal tumors. See Naor et al., CD44: structure, function and association with the malignant process. Adv. Cancer Res. 1997, 71:241-319. Hyaluronic acid HA is synthesized by cells as a high molecular weight form (HMWHA, 1000 to 8000 kDa) and then degraded into low molecular weight fragments (LMWHA, 20 to 250 kDa) by hyaluronidase II (Hyal 2). LMWHA interacts with CD44 receptor for internalization into endosomes/lysosomes and degradation into oligomeric HA (oligo-HA) by hyaluronidase I (Hyal 1). The level of HA in the blood is low and present as a LMW HA form (100-300 kDa) that is cleared out by sinusoid endothelial cells and macrophages in the liver.

Hyaluronic acid nanoparticles may be producing using LMWHA. Hydrophobic patches contribute to the formation stable secondary structures and prevention of nonspecific interactions with proteins and cells. The anti-fouling and viscoelastic features of HA offer advantages for the production of nanoparticle drug carriers. Interactions of HA with cell receptors in tumor stroma and HA-binding proteins in extracellular matrix are believed to contribute to trafficking of HANPs through tumor stroma.

Inhibition of NOX1/4 Improves Resistance to Chemo- and Radiotherapy in Cancer Cells This disclosure relates to nanoparticles containing an anticancer agent such as NADPH oxidase (NOX) inhibitors for targeted delivery to cancerous cells or tumors. In certain embodiments, the anti-cancer agent is a NADPH oxidase (NOX) 1/4 inhibitor such as is 2-(2-chlorophenyl)-4-(3-(dimethylamino)phenyl)-5-methyl-1,2-dihydro-3H-pyrazolo[4,3-c]pyridine-3,6(5H)-dione (GKT831), derivative, or salt thereof.

In certain embodiments, the nanoparticles are administered prior to, during, or after administration of the cancer treatment. In certain embodiments, the cancer treatment is radiation. In certain embodiments, the cancer is breast, lung, brain, pancreatic, colon, or prostate cancer. In certain embodiments, the subject is human.

Many cancer patients received radiation therapy and/or chemotherapy at some point during the course of their treatment. For cancer patients with advanced diseases that are not surgically resectable, radiotherapy and/or chemotherapy are the most common treatment. The vast majority of pancreatic cancer patients are diagnosed at an advanced stage that are unresectable. Treatment options are typically limited to chemotherapy, along with radiotherapy. Pancreatic cancer patients with locally advanced diseases may be treated with the combination of 5-fluorouricil, irinotecan, oxaliplatin, and folinic acid, with or without radiotherapy. Resistance to therapy is the major cause of cancer mortality. Furthermore, normal tissue toxicity limits radiation dose to tumor cells. Radiotherapy induced tissue fibrosis due to inflammation can lead to adverse effects of cardiovascular diseases and irreversible lung injury. Therefore, the development of a radiosensitizer may improve therapeutic responses when in combination with a low irradiation dose avoiding normal tissue damage.

A balance between reactive oxygen species (ROS) production and their neutralization via antioxidants leads to redox homeostasis in cells. Cancer cells generate a high level of ROS, which play important roles in tumorigenesis, metastasis and resistance to therapy. Chronic upregulation of intracellular ROS induces alterations in signal pathways regulating cell proliferation and survival, metabolic reprogram in tumor cells, and inflammation that contribute to resistance to chemo- and radiotherapy. NOX and the mitochondria are the major sources of ROS production. NOX enzyme family consists of seven transmembrane proteins (NOX1-5 and Duox1-2) with similar but distinct structural, biochemical, and subcellular localization characteristics.

NOX1 is located in the plasma membrane and endosomes. It generates superoxide anion ($O_2 \cdot -$). NOX4 is detected in the cellular membrane of focal adhesions, nucleus, endoplasmic reticulum, and mitochondria. It generates intracellular hydrogen peroxide ($H_2O_2$). Upregulation of NOX4 is considered to be the major driver for inflammation induced proliferation of fibroblasts and fibrosis. The levels of NOX1 and NOX4 are upregulated in many human cancer types, including pancreatic and breast cancer, and are associated with tumor progression, metastasis and poor therapeutic response. Upregulation of NOX makes tumor cells better cope with redox imbalance by promoting activation of MAPK, PI3K, NF-κB, and JAK/Stat pathways, and anti-oxidative enzymes, reducing sensitivity to DNA damaging drugs and radiation therapy. NOX-induced ROS has also been recognized as an important factor involved in regulation of cancer stem cells, which is a therapy resistant cell population. Small molecule NOX1 and NOX4 inhibitors have been reported as effective in animal tumor models. Setanaxib (GKT831) is a dual NOX1/NOX4 inhibitor being evaluated for the treatment of pulmonary fibroblasts, primary biliary cholangitis, and kidney fibrosis.

Hyaluronic acid nanoparticles (HANPs) encapsulated GKT831 were prepared. The effects of these nanoparticles when exposed to proliferating tumor cells were examined. Treatment with HANPs/GKT831 alone had a modest tumor growth inhibition. However, the combination of HANPs/GKT831 with chemotherapy drugs or radiation therapy significantly enhanced the effect of tumor growth inhibition in human breast PDX tumor models. Further analysis of gene expression profiles revealed that HANPs/GKT831 was implicated in many oncogenic pathways. Importantly, genes in the DNA repair pathway were markedly downregulated. Gene expression of many key molecules in cell proliferation, cell cycle, survival and inflammation signal pathways were inhibited by HANPs/GKT831 and the combination therapy of HANPs/GKT831 with doxorubicin (Dox) or radiation. Conventional GKT831 treatment had a weaker inhibitory effect on the signal molecules and pathways compared to HANPs/GKT831 treated tumors.

Targeted Protease Compositions and Conjugated Nanoparticles

In certain embodiments, nanoparticles disclosed herein may be conjugated to targeting molecules and may optionally be linked to anti-cancer agents and fluorescent dyes. In certain embodiments, the targeting molecule binds uPAR, EGFR, or HER-2, PMSA, IGF-1R, folate receptor, transferrin receptor, MUC-1, integrin alpha-v beta-3, cell surface nucleolin, CTLA-4, or VEGFR. In certain embodiments, the targeting molecule is an antibody or antibody mimetic, or aptamer of a natural ligand thereof such as the amino-terminal fragment of uPA, EGF, or folic acid.

In one example, nanoparticles are targeted to urokinase plasminogen activator receptor (uPAR), which is a cell surface receptor that is highly expressed in tumor endothelial, stromal fibroblasts and active macrophages, and cancer cells. Methods for carrying various therapeutic agents in or on the nanoparticles are contemplated.

In certain embodiments, the disclosure relates to compositions comprising conjugates comprising a targeting molecule and a protease polypeptide. Typically, the conjugate is linked to a nanoparticle. In certain embodiments, the targeting molecule is linked to the nanoparticle and the protease polypeptide is linked to the nanoparticle.

In certain embodiments, the disclosure relates to nanoparticles comprising a recombinant fusion polypeptide comprising a human uPA sequence or segment thereof configured to bind urokinase plasminogen activator receptor (uPAR) and a human metalloprotease sequence or segment thereof configured to catalyze the degradation of an extracellular matrix protein such as, but not limited to, MMP14, MMP15, MMP16, and MMP17, metalloelastase (MMP12), collegenases (MMP1, MMP8, MMP13), gelatinases (MMP2, MMP9), stromelysins (MMP3, MMP10, MMP11), matrilysin (MMP7, MMP26), enamelysin (MMP20). Typically, the catalytic domain forming the active site comprises a zinc-binding motif of three histidine residues found in the conserved sequence HEXXHXXGXXH (SEQ ID NO: 5) wherein X is individually at each occurrence any amino acid.

An example is the uPA-ATF68-MMP14$_{CD}$ protein sequence (SEQ ID NO: 4). The bold portion is the AFT68 segment, amino acids 2-69 (SEQ ID NO:2) and segment after, i.e., amino acids 71-246 including the bold zinc binding domain, is the MMP14$_{CD}$ (SEQ ID NO: 3):

(SEQ ID NO: 4)
MSNELHQVPSNCDCLNGGTCVSNKYFSNIHWCNCP

KKFGGQHCEIDKSKTCYEGNGHFYRGKASTDTMGA

PIQGLKWQHNEITFCIQNYTPKVGEYATYEAIRKA

FRVWESATPLRFREVPYAYIREGHEKQADIMIFFA

```
EGFHGDSTPFDGEGGFLAHAYFPGPNIGGDTHFDS

AEPWTVRNEDLNGNDIFLVAVHELGHALGLEHSSD

PSAIMAPFYQWMDTENFVLPDDDRRGIQQLYGGES

G.
```

In certain embodiments, the disclosure relates to nanoparticles disclosed herein comprising polypeptides comprising a human uPA sequence or segment thereof configured to bind urokinase plasminogen activator receptor which comprises SEQ ID NO: 2 or a polypeptide with greater than 30% sequence identity or similarity thereto and a catalytic domain of a protease polypeptide which comprises SEQ ID NO: 3 or a polypeptide with greater than 30% sequence identity or similarity thereto.

In certain embodiments, the disclosure relates to nanoparticles disclosed herein comprising or consisting of SEQ ID NO: 4, variants, or sequences with greater than 30%, 40%, 50%, 60%, 70%, 80%, 90%, or 95% sequence identity or similarity thereto.

In certain embodiments, the disclosure relates to nanoparticles disclosed herein comprising or consisting of a human uPA fragment sequence of less than 135, 100, 90, 80, 70, 60, 50, 40, 30 amino acids, e.g., SEQ ID NO: 2, variants, or sequences with greater than 30%, 40%, 50%, 60%, 70%, 80%, 90%, or 95% sequence identity or similarity thereto and a catalytic domain of a human matrix metalloprotease, e.g., SEQ ID NO: 3, variants, or sequences with greater than 30%, 40%, 50%, 60%, 70%, 80%, 90%, or 95% sequence identity or similarity thereto.

In certain embodiments, the fusion polypeptides disclosed herein may contain one or more linking groups or amino acid spacers between the targeting sequence and the protease sequence.

In certain embodiments, nanoparticles disclosed herein may be labeled with a near-infrared (NIR) dye on the thiol-group of cysteine residues. uPA-ATF68-MMP14$_{CD}$ may contain a his-tag at the C-terminus or N-terminus. uPA-ATF68-MMP14$_{CD}$ may conjugated to nanoparticles disclose herein through alternative methods, e.g., 1) affinity binding to a surface polymer with NTA-Cu functional groups or 2) direct conjugation of amine groups of targeting peptides with carboxyl groups on the nanoparticle surface via an amide bond.

In certain embodiments, nanoparticles disclosed herein comprise a lysosomally degradable molecule linked to a therapeutic agent, e.g., wherein degradable molecule is the polypeptide GFLG (SEQ ID NO: 1) linked to the therapeutic agent. See Lee et al. report engineered urokinase plasminogen activator receptor (uPAR)-targeted magnetic iron oxide nanoparticles (IONPs) carrying chemotherapy drug gemcitabine (Gem) for targeted delivery into uPAR-expressing tumor and stromal cells. ACS Nano, 2013, 7(3):2078-89.

In certain embodiments, a near infrared dye can be conjugated to the protease-linked targeting ligands and nanoparticles, providing optical imaging capability. In certain embodiments, the dye is a (3,3-dimethyl-indol-1-ium-1-yl)-N-alkylsulfonate dye or salt thereof such as one of the formula:

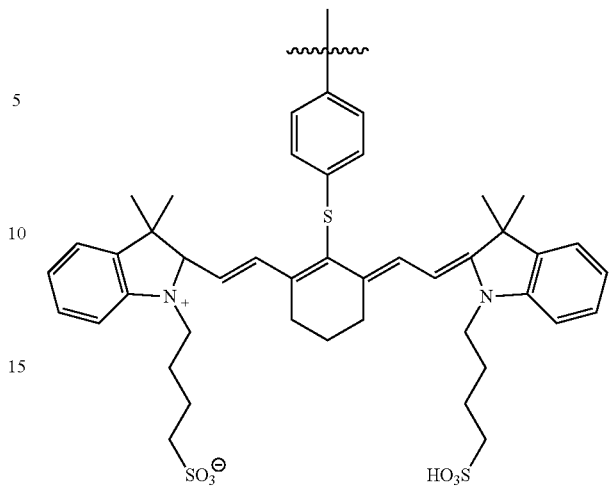

or salts or derivatives thereof optionally substituted with one or more substituents.

In certain embodiments, a fluorescent moiety is linked to the protease conjugate or linked to the nanoparticle. In certain embodiments, the fluorescent moiety is a fluorescent dye, for example, NIR-830 dye, or a fluorescent protein, for example, green fluorescent protein.

Pharmaceutical Compositions

In certain embodiments, the disclosure relates to pharmaceutical compositions comprising particles disclosed herein and a pharmaceutically acceptable excipient. In certain embodiments, the composition is a pill or in a capsule or the composition is liquid solution such as an aqueous buffer, e.g., a pH of about 6.5, 7.0, or 7.5 or between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents and can also be of such composition that they release the particles in a certain part of the intestinal tract in a delayed manner. Examples of embedding compositions which can be used are polymeric substances and waxes.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of the disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Formulations containing particles described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, MD, 2000, and "Pharmaceutical dosage forms and drug delivery systems," 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins, zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, gums, or cross-linked polymers, such as cross-linked PVP.

Production and Characterization of HANP/GKT831

Pharmaceutical grade hyaluronate (200 kDa) was conjugated with a hydrophobic molecule, 5β-cholanic acid, to form HACA that promotes self-assembly and assisted in loading of hydrophobic drug GKT831. HANP/GKT831 are produced by self-assembling HACA and GKT831 using a high-pressure homogenizer (FIG. 2A). The hydrodynamic size of 200 kDa HA derived HANP/GKT831 were about 197 nm in diameter. The amount of encapsulated GKT831 in the HANP/GKT831 was determined to be 18% (w/w) by HPLC. Growth inhibitory effects were determined in MCF-7 human breast cancer cells with the $IC_{50}$ of 4 µM. Treatment of MCF-7 cells with HANP/GKT831, but not free GKT831, markedly decreased the production of reactive oxygen species (ROS) according to a DCFDA assay (FIG. 2E).

Targeted Delivery of HANP/GKT831 into Breast PDX Tumors.

Therapy resistant breast cancer PDX models were established in nude mice from surgically resected tumor tissues of both hormonal receptor positive (HR+) and triple negative breast cancer patients. Patient VII PDX model was derived tumor from HR+ breast cancer tissue that progressed after neoadjuvant therapy with Dox+ Taxol and adjuvant radiotherapy (50 Gy). Patient IX PDX model was derived from a breast cancer tissue that was resistant to Dox/cyclophosphamide/Taxol therapy and 50 Gy of pre-operative radiation therapy. Both patients developed recurrent tumors and deceased 23 and 25 months after surgery. The PDX tumor models have aggressive tumor cells expressing high levels of CD44 and uPAR. CD44 is the cellular receptor for HA and therefore, HANP can target to CD44+ tumor and stromal cells. A high level of uPAR expression in the PDX indicates that they are also a good model for evaluation of the effect of uPAR targeting ligand conjugated HANP drugs. Large tumor cell nests without blood vessels were found containing necrotic areas, which present a challenge for drug delivery into those areas. The targeted delivery of near-infrared (NIR) 830 dye labeled HANPs in the breast cancer PDX models were examined using optical imaging and histological analysis. Following i.v. injection in tumor bearing nude mice for 24 hours, optical imaging showed a high level of HANP accumulated in tumors. Optical signal was also detected in the liver. Histological analysis of tumor tissues revealed that HANPs were delivered into tumor areas that were away from tumor vessels (CD31+) and enriched in necrotic tumor areas. Co-localization of HANPs with CD44+ tumor cells was also detected. Notably, a large portion of HANP+ cells were not CD68+ macrophages, suggesting that HANPs could avoid non-specific uptake by macrophages. Accumulation of HANPs in the liver was further examined. Only a low percentage of HANPs co-localized with CD68+ or CD163+ macrophages in the liver.

Systemic Administration of HANP/GKT831 Significantly Enhances the Effect of Tumor Growth Inhibition of Co-Delivered DOX in Breast Cancer PDX Models The inhibition of NOX1/4 on tumor growth and sensitization of therapeutic responses to a chemotherapy drug, DOX, were examined in the breast Patient VII and Patient IX PDX models growing in the mammary fat pad of nude mice. Following five weekly i.v. treatments of 5 mg/kg GKT831, equivalent dose of HANP/GKT831, and 5 mg/kg of DOX, significant enhancement of tumor growth inhibition in both PDX models was found. In Patient VII PDX model, the mean tumor volume in the mouse group that received the combination therapy of HANP/GKT831 and DOX showed a 25% decrease compared the starting tumor volume (approximately 250 to 280 $nm^3$). Tumors in the no treatment control, HANP/GKT831 or DOX treatment alone groups, had 150 (Dox) to 250% of increases in tumor volumes compared the starting tumor volumes. Overall, by the end of the study, the mean tumor weight in the combination therapy group was 89% lower than that of no treatment control group. Dox or HANP/GKT831 treatment alone only had intermediate effects on tumor growth inhibition (~40%). DOX alone inhibited tumor growth for 60% compared to the no treatment control.

Histological analysis of proliferating cells (Ki67+) in tumor tissues showed that the combination therapy had inhibited cell proliferation by 96%, while other treatment groups showed ~60% inhibition (FIG. 3C). Similarly, results from an in vivo study in the breast cancer patient IX PDX model showed 86% of tumor growth inhibition in the mouse group that received the combination therapy in comparison with the no treatment control (FIGS. 3D & 3E). HANP/GKT831 or GKT831+DOX treatment reduced tumor volume by 57% (FIG. 3E). In both PDX models, free GKT831 treatment at an equivalent i.v. dose did not show a significant difference in tumor growth inhibition compared to no treatment control, suggesting that the HANP nanoparticle formulation of GKT831 is important for a strong therapeutic effect. Additionally, there was no systemic toxicity found in all experimental mice treated with HANP/GKT831 or the combination therapy.

Combination Treatment of HANPs/GKT831 and Radiation Significantly Enhanced the Response to Radiation in Two Breast Cancer PDX Models Experiments were performed to determine whether inhibition of NOX1/4 prevents tumor growth and sensitize therapeutic responses to radiotherapy (IR) using two IR resistant breast cancer PDX models. Tumors were placed in the mammary fat pad of nude mice. Following five weekly i.v. treatments of 5 mg/kg GKT831, equivalent dose of HANP/GKT831 and 2 Gy radiation was applied 24 hours after each i.v. HANPs/GKT831 delivery. Therapeutic response to IR in tumors was significantly enhanced by the combination with HANP/GKT831 in both breast cancer PDX models. In Patient VII PDX model, the mean tumor volume in the mouse group treated with the combination of HANP/GKT831 and IR was decreased 35% compared to the starting tumor volume (~280 mm³). However, tumors in mouse groups treated with GKT831, HANP/GKT831, IR, or GKT831+IR increased 200 to 240% compared to the starting tumor volumes. There was a significant difference in tumor growth inhibition between the HANP/GKT831+IR group with all other control and treatment groups (p<0.05). Overall growth inhibition in HANP/GKT831+IR treatment group was 87% compared with the no treatment control group (FIGS. 4A & 4B). Histological analysis showed that HANP/GKT831+IR treatment significantly decreased proliferating cells (Ki67+) and increased the apoptotic cell death (active caspase 3+) in tumor tissue (FIGS. 4C & 4E). Immunofluorescence labeling further revealed that HANP/GKT831+IR treatment markedly increased γ-H2AX+ cells in tumor tissues, which is a biomarker for DNA double stranded breaks (FIG. 4D). In breast IX PDX model, the combination treatment of HANP/GKT831 with IR or Dox significantly inhibited tumor growth compared to the no treatment control. Further combination of HANP/GKT831 with co-treatment of Dox and 2 Gy radiation had the strongest tumor growth inhibition among all treatment groups (FIG. 5).

Characterization of HANPs Engineered from Different LMWHAs

The effects of LMWHA on cell proliferation and viability have been controversial because LMWHA is defined by a wide range of HA fragments. To determine the biological effects of HANPs, a method was developed to engineer the size tunable HANPs from 10, 60, 100 and 200 KDa of HAs, resulting in HANPs with hydrodynamic sizes of 45±13, 100.21±27, 135±40 and 18 0±29 nm (FIG. 6A). Treatment of mouse MC38 colon tumor cells with 0.08 to 25 μM of 100 or 200 KDa of native HA fragments did not significantly alter cell proliferation. However, treatment of tumor cells with 0.1 μM of HANPs reduced the percentage of viable tumor cells by 50% ($IC_{50}$). Treatment of tumor cells with smaller MWHA fragments (10 or 60 KDa) at high concentrations modestly increased the percentage of viable cells. HA (200 KDs) were used generated nanoparticle drug carriers at the HA concertation less than 0.035 μM, which by itself, does not affect cell proliferation or viability.

HANP/GKT831 has Significant Different Biological Properties on Human Tumors Compared with GKT831.

Biomaterial low molecular weight HA generated nanoparticle drug carrier has unique biological activities compared with other nanoparticle drug carriers. HANP/GKT831 not only improves intratumoral delivery of GKT831 but also showed differential regulation of signal pathways that are critical for cancer cell survival, proliferation, metastasis, and DNA damage repair that lead to resistance to chemotherapy and radiotherapy (FIG. 7). To understand molecular mechanisms by which HANP/GKT831 enhanced responses to DNA damaging drug and radiation, gene expression profiles of the breast patient VII PDX tumors following five i.v. treatments were analyzed using RNAseq assay. HANP/GKT831 had stronger inhibition on NOX1 than that of GKT831. Both did not significantly affect the level of NOX4 gene expression, suggesting that NOX4 inhibition was mediated by inhibiting its function. However, GKT831 downregulated NOX2 but HANP/GKT831 slightly upregulated NOX2. Since human immune cells express NOX2 subtype, HANP/GKT831 treatment may not affect tumor immune responses but GKT831 treatment may decrease immune responses in tumors. Furthermore, HANP/GKT831 inhibited the expression of mitochondrial electron transport and ATP production genes, which promote tumor cell death (FIG. 7B). On the other hand, GKT 831 treatment upregulated the expression of some of those genes and had a minimal effect on many other gene (FIG. 7B). HANP/GKT831 treatment also significantly inhibited the levels of expression of the majority of DNA repairing genes to enhance tumor cell response to DNA damaging drugs and radiotherapy (FIG. 7C). Importantly, HANP/GKT831 has a stronger inhibitory effect on the levels of expression of oncogenic genes and signal pathway genes that activate cell proliferation and survival (FIG. 7D). Therefore, it is likely that those differences in gene regulation contributed to a strong chemo- and radiotherapy enhancement effect of HANP/GKT831.

HANP/GKT831 is a novel agent that has the potential to be developed as a dual chemotherapy and radiotherapy sensitizer for effective treatment of therapy resistant cancer patients by the combination of chemotherapy or radiotherapy with HANP/GKT831. As NOX1/4 inhibition reduces inflammation and fibrosis, it is feasible to develop HANP/GKT831 as an enhancer for chemoradiotherapy that is currently used in the clinic for the treatment of pancreatic, rectal, liver, and head and neck cancer. The possibility of decreasing in radiotoxicity to the lung and heart as well as systemic toxicity of chemotherapy drugs by HANP/GKT831 treatment allows for combined chemotherapeutic and radio-therapeutic approaches. This treatment is contemplated to be particularly beneficial for patients diagnose with advanced breast cancer, e.g., diagnose with local recurrent tumor and distant metastases; colon cancer diagnose with liver metastases; and lung cancer.

Effects of Particle Size and Surface Modification on Receptor Binding and Internalization of HANPs/GKT831 in Tumor Cells, Endothelial Cells and Macrophages In Vitro Although HANPs can bind to CD44 receptor for targeted delivery, specifically designed conjugation of tumor targeting short peptides will be examined for improved HANPs/drug delivery. uPAR is highly expressed in the invasive cancer cells and tumor stromal cells as well as angiogenic endothelial cells but its level is very low in normal tissues. uPAR is expressed in a similar cell types as CD44 and can efficiently internalize nanoparticle/drug complexes. ATF24 (24 aa) and ATF65 (65 aa) peptides may be synthesized and conjugated to the surface of HANPs as outlined in FIG. 8.

What is claimed is:

1. A method of treating breast cancer comprising administering an effective amount of a nanoparticle in combination with doxorubicin and radiation to a subject in need thereof; wherein the nanoparticle comprises 5β-cholanic acid conjugated to hyaluronic acid and 2-(2-chlorophenyl)-4-(3-(dimethylamino)phenyl)-5-methyl-1,2-dihydro-3H-pyrazolo[4,3-c]pyridine-3,6 (5H)-dione or salt thereof.

2. The method of claim 1, wherein the subject is human.

* * * * *

SEQUENCE LISTING

<160> NUMBER OF SEQ ID NOS: 11

<210> SEQ ID NO 1
<211> LENGTH: 4
<212> TYPE: PRT
<213> ORGANISM: Artificial
<220> FEATURE:
<223> OTHER INFORMATION: Synthetic construct

```
<400> SEQUENCE: 1

Gly Phe Leu Gly
1

<210> SEQ ID NO 2
<211> LENGTH: 68
<212> TYPE: PRT
<213> ORGANISM: Artificial
<220> FEATURE:
<223> OTHER INFORMATION: Synthetic construct

<400> SEQUENCE: 2

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly
65

<210> SEQ ID NO 3
<211> LENGTH: 11
<212> TYPE: PRT
<213> ORGANISM: Artificial
<220> FEATURE:
<223> OTHER INFORMATION: Synthetic construct

<400> SEQUENCE: 3

His Glu Leu Gly His Ala Leu Gly Leu Glu His
1               5                   10

<210> SEQ ID NO 4
<211> LENGTH: 246
<212> TYPE: PRT
<213> ORGANISM: Artificial
<220> FEATURE:
<223> OTHER INFORMATION: Synthetic construct

<400> SEQUENCE: 4

Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Lys Ser
        35                  40                  45

Lys Thr Cys Tyr Glu Gly Asn Gly His Phe Tyr Arg Gly Lys Ala Ser
    50                  55                  60

Thr Asp Thr Met Gly Ala Pro Ile Gln Gly Leu Lys Trp Gln His Asn
65                  70                  75                  80

Glu Ile Thr Phe Cys Ile Gln Asn Tyr Thr Pro Lys Val Gly Glu Tyr
                85                  90                  95

Ala Thr Tyr Glu Ala Ile Arg Lys Ala Phe Arg Val Trp Glu Ser Ala
            100                 105                 110

Thr Pro Leu Arg Phe Arg Glu Val Pro Tyr Ala Tyr Ile Arg Glu Gly
        115                 120                 125

His Glu Lys Gln Ala Asp Ile Met Ile Phe Phe Ala Glu Gly Phe His
    130                 135                 140
```

```
Gly Asp Ser Thr Pro Phe Asp Gly Glu Gly Gly Phe Leu Ala His Ala
145                 150                 155                 160

Tyr Phe Pro Gly Pro Asn Ile Gly Gly Asp Thr His Phe Asp Ser Ala
            165                 170                 175

Glu Pro Trp Thr Val Arg Asn Glu Asp Leu Asn Gly Asn Asp Ile Phe
            180                 185                 190

Leu Val Ala Val His Glu Leu Gly His Ala Leu Gly Leu Glu His Ser
            195                 200                 205

Ser Asp Pro Ser Ala Ile Met Ala Pro Phe Tyr Gln Trp Met Asp Thr
210                 215                 220

Glu Asn Phe Val Leu Pro Asp Asp Arg Arg Gly Ile Gln Gln Leu
225                 230                 235                 240

Tyr Gly Gly Glu Ser Gly
                245

<210> SEQ ID NO 5
<211> LENGTH: 11
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 5

His Glu Xaa Xaa His Xaa Xaa Gly Xaa Xaa His
1               5                   10

<210> SEQ ID NO 6
<211> LENGTH: 28
<212> TYPE: PRT
<213> ORGANISM: Artificial
<220> FEATURE:
<223> OTHER INFORMATION: Synthetic construct

<400> SEQUENCE: 6

Cys His His His Cys Leu Asn Gly Gly Thr Cys Val Ser Asn Lys Tyr
1               5                   10                  15

Phe Ser Asn Ile His Trp Cys Asn Cys Pro Lys Lys
            20                  25

<210> SEQ ID NO 7
<211> LENGTH: 66
<212> TYPE: PRT
<213> ORGANISM: Artificial
<220> FEATURE:
<223> OTHER INFORMATION: Synthetic construct

<400> SEQUENCE: 7

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30
```

```
Cys Pro Lys Lys Phe Gly Gly Gln His Cys Glu Ile Asp Lys Ser Lys
            35                  40                  45
Thr Cys Tyr Glu Gly Asn Gly His Phe Tyr Arg Gly Lys Ala Ser Thr
 50                  55                      60
Asp Cys
 65

<210> SEQ ID NO 8
<211> LENGTH: 6
<212> TYPE: PRT
<213> ORGANISM: Artificial
<220> FEATURE:
<223> OTHER INFORMATION: Synthetic construct

<400> SEQUENCE: 8

Gly Gly Gly Gly Gly Gly
1               5

<210> SEQ ID NO 9
<211> LENGTH: 5
<212> TYPE: PRT
<213> ORGANISM: Artificial
<220> FEATURE:
<223> OTHER INFORMATION: Synthetic construct

<400> SEQUENCE: 9

Gly Gly Gly Gly Thr
1               5

<210> SEQ ID NO 10
<211> LENGTH: 6
<212> TYPE: PRT
<213> ORGANISM: Artificial
<220> FEATURE:
<223> OTHER INFORMATION: Synthetic construct

<400> SEQUENCE: 10

Gly Gly Gly Pro Pro Pro
1               5

<210> SEQ ID NO 11
<211> LENGTH: 7
<212> TYPE: PRT
<213> ORGANISM: Artificial
<220> FEATURE:
<223> OTHER INFORMATION: Synthetic construct

<400> SEQUENCE: 11

Gly Gly Gly Ala Pro Pro Pro
1               5
```